US012791541B2

(12) United States Patent
Fujiwara et al.

(10) Patent No.: US 12,791,541 B2
(45) Date of Patent: Nov. 10, 2026

(54) DETERMINATION METHOD AND DETERMINATION DEVICE FOR LASER PROCESSING STATE

(71) Applicant: Panasonic Intellectual Property Management Co., Ltd., Osaka (JP)

(72) Inventors: Kazuki Fujiwara, Osaka (JP); Koji Funami, Kyoto (JP); Izuru Nakai, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 586 days.

(21) Appl. No.: 18/233,954

(22) Filed: Aug. 15, 2023

(65) Prior Publication Data

US 2023/0384282 A1 Nov. 30, 2023

Related U.S. Application Data

(63) Continuation of application No. PCT/JP2022/000132, filed on Jan. 5, 2022.

(30) Foreign Application Priority Data

Feb. 26, 2021 (JP) ................................ 2021-029936

(51) Int. Cl.
*G01N 33/207* (2019.01)
*G01N 21/95* (2006.01)

(52) U.S. Cl.
CPC ........... *G01N 33/207* (2019.01); *G01N 21/95* (2013.01)

(58) Field of Classification Search
None
See application file for complete search history.

(56) References Cited

U.S. PATENT DOCUMENTS

| | | | | |
|---|---|---|---|---|
| 2011/0023610 | A1* | 2/2011 | Ume | G01N 29/11 73/622 |
| 2015/0001196 | A1* | 1/2015 | Kim | B23K 31/125 219/121.83 |
| 2017/0032281 | A1 | 2/2017 | Hsu | |

FOREIGN PATENT DOCUMENTS

| | | |
|---|---|---|
| JP | 11058046 | 3/1999 |
| JP | 2000-153379 | 6/2000 |
| JP | 2005-172559 | 6/2005 |

(Continued)

*Primary Examiner* — Matthew G Marini
(74) *Attorney, Agent, or Firm* — Wenderoth, Lind & Ponack, L.L.P.

(57) ABSTRACT

A determination method for determining a processing state includes detecting, using an optical sensor, at least one of heat radiation light, visible light, and reflected light generated at a welded portion formed at a surface of a workpiece by emission of a laser beam on the workpiece, obtaining, from the optical sensor, a signal indicating a change in one of heat radiation, visible light, and reflected light in a time section corresponding to a welding time of each workpiece, determining, as the processing state, the position and number of molten shape abnormality in a welded region having a molten length and a molten width by inputting a feature quantity to a determination model that determines the processing state, the feature quantity including signal intensity of the signal, the molten shape abnormality occurring when a foreign substance exists at an overlapping surface of the workpiece, and outputting a determination result.

8 Claims, 10 Drawing Sheets

(56) References Cited

FOREIGN PATENT DOCUMENTS

| | | | | |
|---|---|---|---|---|
| JP | 4491996 | B2 | * | 6/2010 |
| JP | 2010-249685 | | | 11/2010 |
| JP | 2017-177171 | | | 10/2017 |
| JP | 2020-189305 | | | 11/2020 |
| WO | 2012/000648 | | | 1/2012 |

* cited by examiner

DETERMINATION METHOD AND DETERMINATION DEVICE FOR LASER PROCESSING STATE

TECHNICAL FIELD

The present disclosure relates to a determination method and a determination device for determining a processing state in laser processing for lap welding.

BACKGROUND ART

Unexamined Japanese Patent Publication No. 2000-153379 (hereinafter, "JP '379") discloses a determination method for determining a welding state in laser welding, the method being applied to a laser welding method of welding by emitting a pulsed laser beam on a workpiece and used for determining whether a welding state of the workpiece is good or poor, for example. In the method in JP '379, the intensity of plasma light and reflected light emitted from the workpiece during laser welding is detected as detection light intensity, and a feature value of each pulse is extracted for each pulse of the laser beam based on the detection light intensity in an extraction section preset in a single cycle of the detection light intensity corresponding to a single pulse of the laser beam. As the feature value of each pulse, an average of the detection light intensity, a change amount resulting from difference processing, and an amplitude resulting from difference processing are calculated, for example. In the method in JP '379, the lowest value or the highest value of the feature value of each pulse is obtained as an extreme value, the extreme value is compared with a predetermined threshold value, and whether a welding defect has occurred is determined as a welding state of each workpiece.

SUMMARY OF THE INVENTION

According to one aspect of the present disclosure, a determination method for determining a processing state in laser processing for lap welding is provided. The present method includes detecting, using an optical sensor, at least one of heat radiation light, visible light, and reflected light generated at a welded portion formed at a surface of a workpiece by emission of a laser beam on the workpiece, obtaining, from the optical sensor, a signal indicating a change in one of heat radiation, visible light, and reflected light in a time section corresponding to a welding time of each workpiece, determining, as the processing state, the position and number (quantity) of molten shape abnormalities in a welded region having a molten length and a molten width by inputting a feature quantity to a determination model that determines the processing state. The feature quantity includes a signal intensity of the signal based on the signal, and the molten shape abnormality occurs when a foreign substance exists at an overlapping surface of the workpiece, and the determined position and number (quantity) of molten shape abnormalities is output as a determination result. The determination model is constructed based on training data including the feature quantity calculated under a condition where the molten shape abnormality occurs and the processing state in the condition where the molten shape abnormality occurs.

According to one aspect of the present disclosure, a determination device for determining a processing state in laser processing for lap welding is provided. The determination device includes an arithmetic circuit and a communication circuit. The communication circuit receives a signal generated by detecting, by an optical sensor, at least one of heat radiation light, visible light, and reflected light generated at a welded portion formed at a surface of a workpiece by emission of a laser beam on the workpiece. The signal indicates a change in at least one of heat radiation, visible light, and reflected light in a time section corresponding to a welding time of each workpiece. The arithmetic circuit obtains a signal by the communication circuit, determines, as the processing state, the position and number of molten shape abnormality in a welded region having a molten length and a molten width by inputting a feature quantity to a determination model that determines the processing state, the feature quantity including signal intensity of a signal based on the signal, the molten shape abnormality occurring when a foreign substance exists at an overlapping surface of the workpiece, and outputs by the communication circuit, as a determination result, the determined position and number of molten shape abnormalities. The determination model is constructed based on training data including the feature quantity calculated under a condition where the molten shape abnormality occurs and the processing state in the condition where the molten shape abnormality occurs.

DESCRIPTION OF EMBODIMENT

In laser welding, for example, when dirt or a foreign substance exists on a workpiece, abnormality in molten shape such as a hole formed in a welded portion may occur during lase emission. In a method for determining occurrence of a welding defect by a threshold, existence or non-existence of such abnormality can be determined, but it is difficult to determine a detailed processing state such as the number (quantity) and position of molten shape abnormalities.

The present disclosure provides a determination method and a determination device capable of determining in detail a processing state in laser processing for lap welding.

Exemplary embodiments will be described below in detail with reference to the drawings as appropriate. However, unnecessarily detailed description may be omitted. For example, detailed description of already well-known matters and repeated description of substantially the same configurations may be omitted. These are to avoid an unnecessarily redundant description and to facilitate understanding of a person skilled in the art. Note that, the attached drawings and the following description are presented by the inventor so that those skilled in the art can fully understand the present disclosure, and are not intended to limit the subject matter as described in the claims.

First Exemplary Embodiment

In a first exemplary embodiment, as an example of using a determination method and a determination device according to the present disclosure, a determination system will be described that detects a component of light generated in laser processing for lap welding, obtains a signal based on the detected component, and determines a processing state.

1. Configuration

Figure 1:
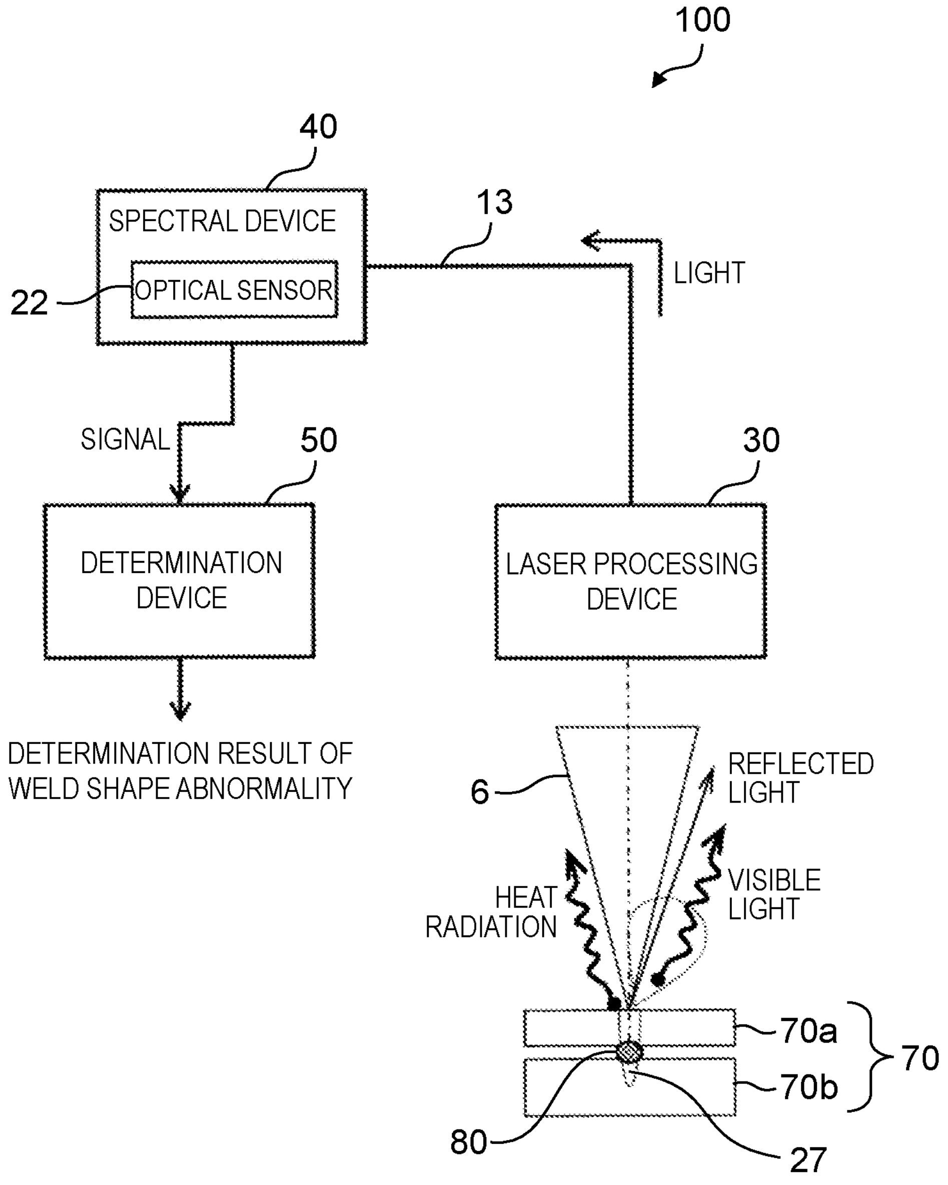
FIG. 1 is a diagram illustrating an overview of a determination system according to a first exemplary embodiment of the present disclosure.

The determination system according to the first embodiment will be described with reference to FIG. 1. FIG. 1 is a diagram illustrating an overview of determination system 100 according to the exemplary embodiment.

1-1. System Overview

Determination system 100 includes laser processing device 30 that performs laser processing for lap welding, spectral device 40 for detecting a component of light, and determination device 50. Determination device 50 is an example of the determination device according to the present disclosure. Workpiece 70 subjected to lap welding is made of, for example, a metal. Emission of laser beam 6 on workpiece 70 generates heat radiation light (also referred to as "heat radiation") in a near-infrared light region due to a temperature rise and causes light emission specific to metal or plasma light emission, both light emissions mainly containing visible light. A portion of laser beam 6 that does not contribute to the processing is reflected to be a return light. As described above, emission of laser beam 6 by laser processing device 30 on workpiece 70 generates heat radiation, visible light, and reflected light at molten portion 27 formed in workpiece 70. Molten portion 27 is an example of a welded portion of the present exemplary embodiment.

Under emission of laser beam 6, if, for example, foreign substance 80 made of a carbon-based material such as resin or oil exists between two members 70*a*, 70*b* constituting workpiece 70, a molten shape abnormality such as a hole or a protrusion in a welded region occurs. The welded region is a region that remains as a mark of molten portion 27 after processing at a surface of member 70*a* on the side to laser processing device 30 and has a molten length that is a length in a direction in which the welding processing progresses and a molten width that is a width in a direction perpendicular to the progressing direction of the weld processing. Light emission also occurs at molten portion 27 due to melting of foreign substance 80 existing at an overlapping surface of workpiece 70.

The light generated at molten portion 27 is condensed in laser processing device 30 and transmitted to spectral device 40 through optical fiber 13 connecting laser processing device 30 to spectral device 40. The light transmitted to spectral device 40 is dispersed into heat radiation, visible light, and reflected light that are then detected by optical sensor 22 of spectral device 40 and converted into signals. Upon receiving a signal from spectral device 40, determination device 50 according to the present exemplary embodiment determines, as a processing state, the position and number (quantity) of molten shape abnormalities that manifests in a form of a hole, for example, and the size of molten shape abnormality, and outputs the determination result.

1-2. Configuration of Laser Processing Device

Figure 2:
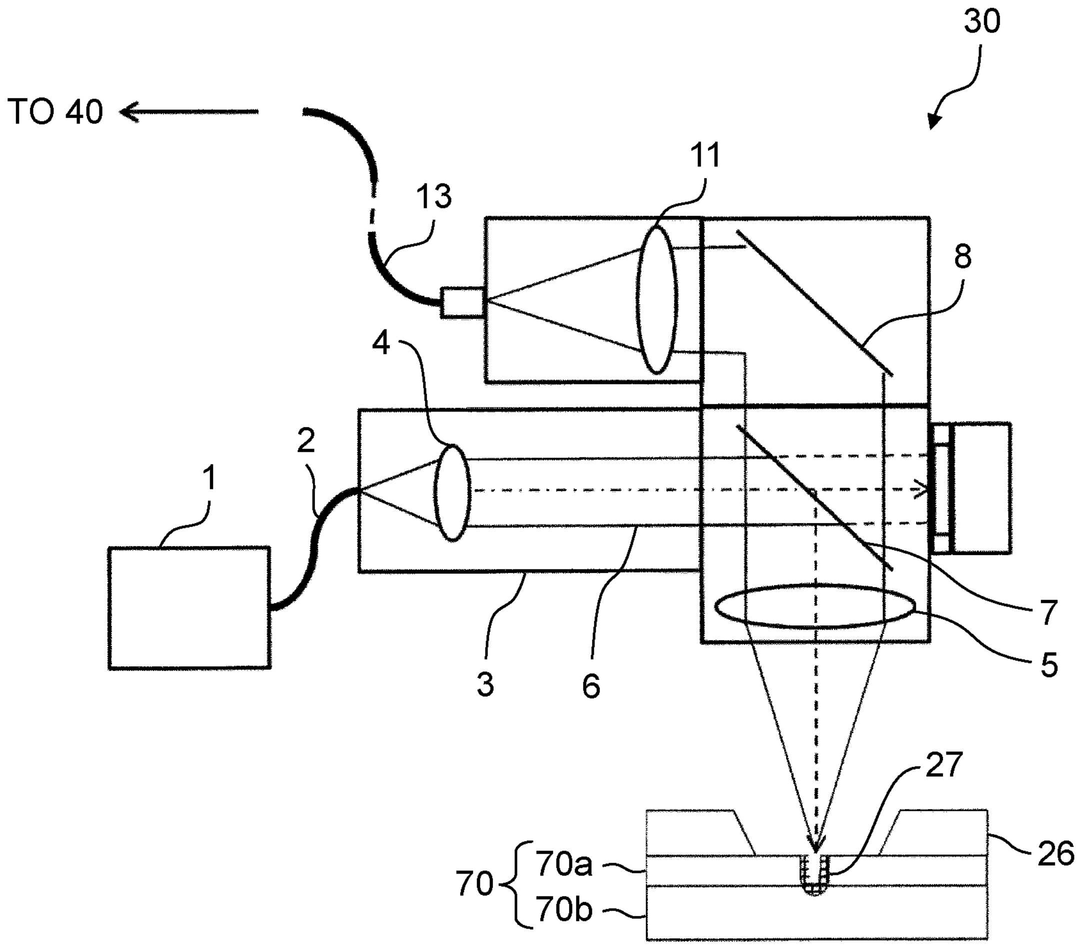
FIG. 2 is a diagram illustrating a configuration of a laser processing device of the determination system.

FIG. 2 is a diagram illustrating a configuration of laser processing device 30 of the present exemplary embodiment. Laser processing device 30 includes laser oscillator 1, laser transmission fiber 2, lens barrel 3, collimating lens 4, condenser lenses 5 and 11, first mirror 7, and second mirror 8.

Laser oscillator 1 supplies light for generating pulsed laser beam 6 having a wavelength of, for example, about 1070 nanometers (nm). The light supplied from laser oscillator 1 is amplified while being transmitted through laser transmission fiber 2, passes through collimating lens 4 for obtaining a parallel beam, forms into laser beam 6, and travels straight in lens barrel 3. Lens barrel 3 constitutes a processing head of laser processing device 30.

Laser beam 6 is reflected by first mirror 7 except for a portion passing through first mirror 7, and reflected laser beam 6 is condensed by condenser lens 5 and emitted on workpiece 70 fixed on a scanning table (not illustrated) by hold jig 26, for example. Laser processing for lap welding of workpieces 70 is thereby performed. The wavelength of laser beam 6 is not particularly limited to 1070 nm. A wavelength having a high absorption rate in a material is preferably used.

By emission of laser beam 6, heat radiation from workpiece 70, visible light of plasma emission, and reflected light of laser beam 6 are generated at molten portion 27. These lights passes through first mirror 7, reflected by second mirror 8, condensed by condenser lens 11, and then transmitted to spectral device 40 through optical fiber 13. A portion of light that passes through second mirror 8 may be detected by a camera or a sensor.

1-3. Configuration of Spectral Device

Figure 3:
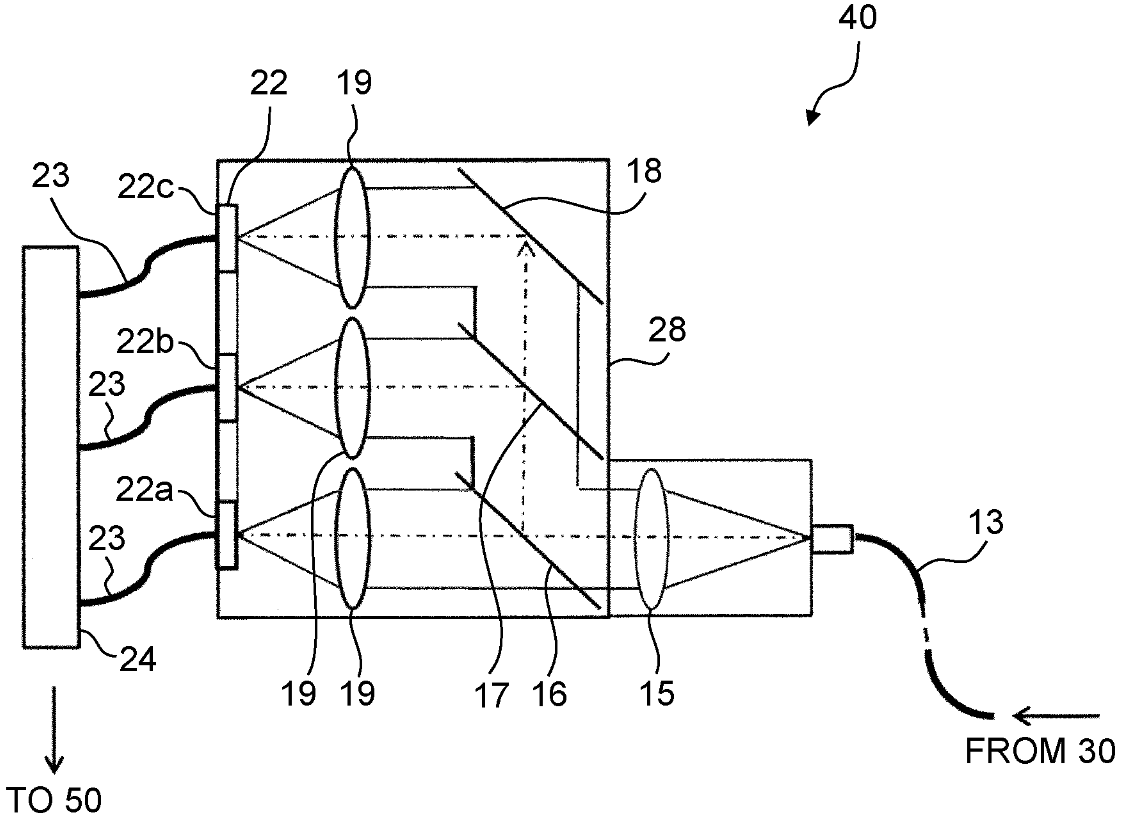
FIG. 3 is a diagram illustrating a configuration of a spectral device of the determination system.

FIG. 3 is a diagram illustrating a configuration of spectral device 40 of the present exemplary embodiment. Spectral device 40 includes, in housing 28, collimating lens 15, third mirror 16, fourth mirror 17, fifth mirror 18, condenser lenses 19, 20, 21, optical sensor 22, transmission cables 23, and controller 24. Housing 28 prevents other lights from entering from outside spectral device 40 and leakage of light from inside spectral device 40.

Collimating lens 15 changes the light transmitted from laser processing device 30 through optical fiber 13 into a parallel light again. Third mirror 16 lets visible light having a wavelength of 400 nm to 700 nm, for example, pass therethrough and reflects the rest of the light components. Fourth mirror 17 reflects the reflected light of laser beam 6 having a wavelength of about 1070 nm, for example, and transmits the rest of the light components. Fifth mirror 18 reflects heat radiation having a wavelength of 1300 nm to 1550 nm, for example.

The light that has passed through collimating lens 15 is dispersed by third mirror 16, fourth mirror 17, and fifth mirror 18 into visible light, reflected light, and heat radiation, and the dispersed lights are each condensed by condenser lenses 19 to 21. Any selected bandpass filter may be disposed in each of the optical paths respectively coming from third mirror 16, fourth mirror 17, and fifth mirror 18 to select a certain wavelength of the light that passes through the bandpass filter.

Optical sensor 22 includes, for example, optical sensors 22*a*, 22*b*, 22*c* each having high sensitivity for a wavelength that differs among optical sensors 22*a*, 22*b*, 22*c*. Optical sensors 22*a*, 22*b*, 22*c* detect visible light, reflected light, and heat radiation condensed by condenser lenses 19 to 21, respectively, and each generate an electric signal corresponding to the intensity of the detected light. Note that, optical sensor 22 may be a single optical sensor capable of detecting the intensity of each wavelength.

The electrical signal generated by optical sensor 22 is transmitted to controller 24 via transmission cables 23. Controller 24 is a hardware controller, and integrally controls all the operations of spectral device 40. Controller 24 includes a CPU and a communication circuit, and transmits the electric signal received from optical sensor 22 to determination device 50. Controller 24 includes, for example, an A/D converter, and converts an analog electric signal into a digital signal (also simply referred to as "signal"). Note that, the sampling period of conversion into a digital signal is preferably, for example, 1/100 or less of a time for performing output control of laser beam 6 from the viewpoint of securing a sufficient number of samples to capture a feature of processing and local behavior of a physical quantity for determining the processing state.

1-4. Configuration of Determination Device

Figure 4:
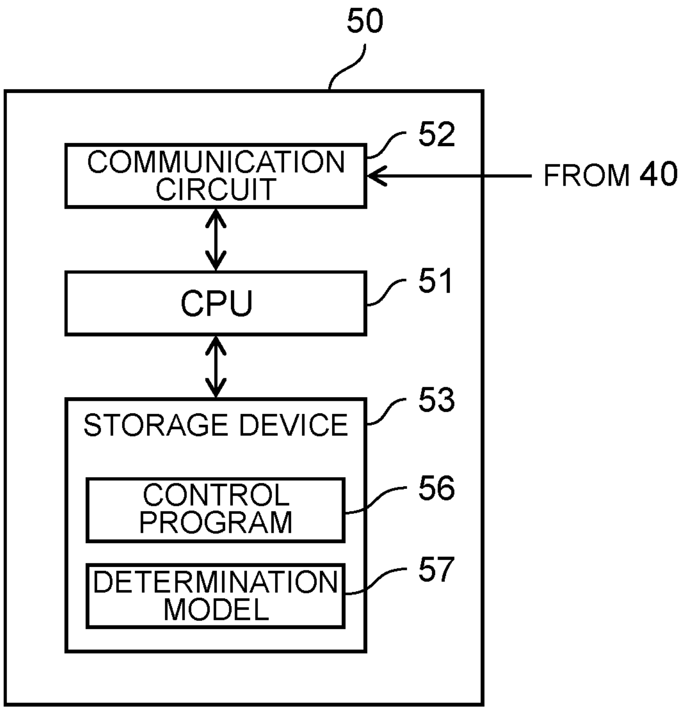
FIG. 4 is a block diagram illustrating a configuration of the determination device of the determination system.

FIG. 4 is a block diagram illustrating a configuration of determination device 50 of the present exemplary embodiment. Determination device 50 is, for example, an information processing device such as a computer. Determination device 50 includes CPU 51 that performs arithmetic processing, communication circuit 52 for communication with other devices, and storage device 53 that stores data and a computer program.

CPU 51 is an example of an arithmetic circuit of the determination device of the present exemplary embodiment. CPU 51 implements predetermined functions including training and execution of determination model 57 by executing control program 56 stored in storage device 53. Determination device 50 implements a function as the determination device of the present exemplary embodiment by CPU 51 executing control program 56. Note that, the arithmetic circuit configured as CPU 51 in the present exemplary embodiment may be implemented by a processor of various kinds such as an MPU and a GPU, or may be configured by one or a plurality of processors.

Communication circuit 52 is a communication circuit that performs communication in accordance with a standard such as IEEE 802.11, 4G, and 5G. Communication circuit 52 may perform wired communication in accordance with a standard such as Ethernet (registered trademark). Communication circuit 52 is connectable to a communication network such as the Internet. Determination device 50 may directly communicate with another device via communication circuit 52, or may communicate via an access point. Note that, communication circuit 52 may be configured to be able to communicate with other devices without a communication network. For example, communication circuit 52 may include a connection terminal such as a USB (registered trademark) terminal and an HDMI (registered trademark) terminal.

Storage device 53 is a storage medium that stores a computer program and data necessary for implementing a function of determination system 100, and stores control program 56 executed by CPU 51 and data of various kinds. After construction of determination model 57, storage device 53 stores determination model 57. Determination model 57 is constructed based on training data including a feature quantity calculated under a condition where the molten shape abnormality occurs and the processing state in which the molten shape abnormality has occurred. Details of determination model 57 will be described later.

Storage device 53 is configured as, for example, a magnetic storage device such as a hard disk drive (HDD), an optical storage device such as an optical disk drive, or a semiconductor storage device such as an SSD. Storage device 53 may include a temporary storage element configured by a RAM such as a DRAM and an SRAM, or may function as an internal memory of CPU 51.

2. Operation

In determination system 100 configured as described above, for example, as illustrated in FIG. 1, spectral device 40 detects by optical sensor 22 heat radiation, visible light, and reflected light generated at molten portion 27 by emission of laser beam 6. Spectral device 40 transmits a signal corresponding to the intensity of the detected heat radiation, visible light, and reflected light to determination device 50. The operation of determination device 50 of the present system 100 will be described below.

2-1. Determination Process

Hereinafter, a determination process of determining the position, number, and size of molten shape abnormality performed by determination device 50 will be described with reference to FIGS. 5 to 8.

Figure 5:
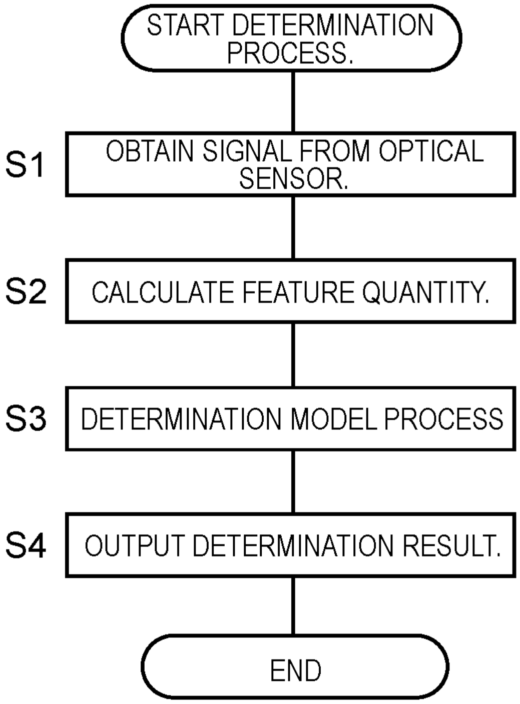
FIG. 5 is a flowchart illustrating a determination process of the determination device.

FIG. 5 is a flowchart illustrating a determination process performed by determination device 50 of the present exemplary embodiment. Each process in the flowchart is executed by, for example, CPU 51 of determination device 50. The flowchart starts by, for example, a user of determination system 100 giving a predetermined manipulation input for starting the determination process to an input device connected via communication circuit 52.

First, CPU 51 obtains, by communication circuit 52, signals corresponding to heat radiation, visible light, and reflected light detected by optical sensor 22 of spectral device 40 (S1).

Figure 6:
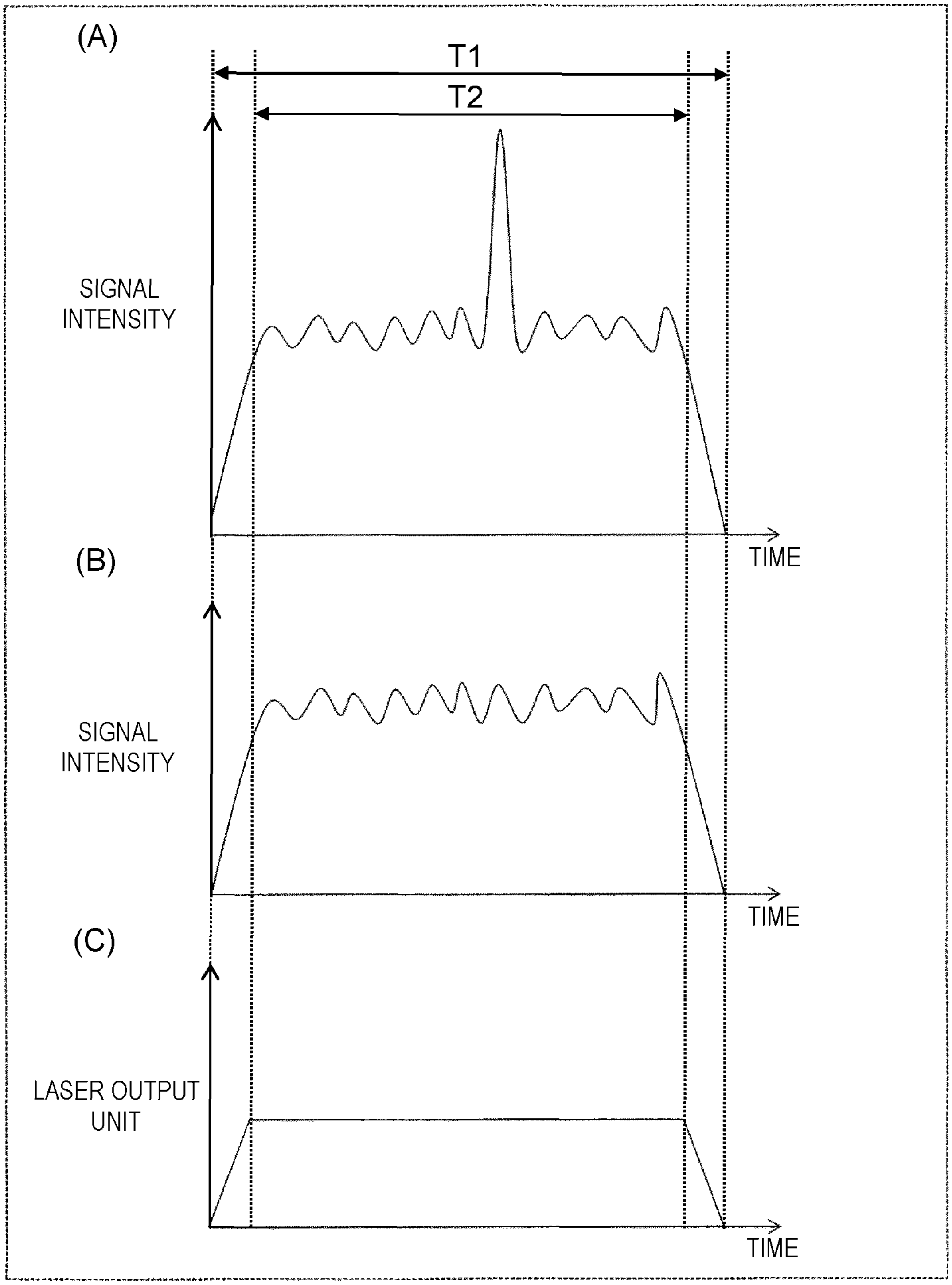
FIG. 6 is a diagram for explaining a signal obtained by the determination device.

FIG. 6 is a diagram for explaining a signal obtained by determination device 50. Part (A) of FIG. 6 illustrates a signal waveform of a signal corresponding to any one of heat radiation, visible light, and reflected light in a case where molten shape abnormality occurs during processing. Part (B) of FIG. 6 illustrates a signal waveform of any one of heat radiation, visible light, and reflected light when no molten shape abnormality occurs. Part (C) of FIG. 6 illustrates an output of laser beam 6 emitted on workpiece 70. Signals in parts (A) and (B) of FIG. 6 each correspond to any one of heat radiation, visible light, and reflected light generated by the laser output in part (C) of FIG. 6.

In each of parts (A) to (C) of FIG. 6, the horizontal axis represents time, and the vertical axis represents signal intensity (in parts (A) and (B) of FIG. 6) or laser output (in part (C) of FIG. 6). Time T1 indicates a time section corresponding to a single pulse of laser beam 6, and time T2 indicates a time section of a peak output not including the rising section and the falling section of the laser output. In laser processing device 30 of the present exemplary embodiment, welding is performed on each workpiece 70 in time T1. In step S1, CPU 51 obtains signals indicating changes in heat radiation, visible light, and reflected light in time T1 corresponding to the welding time of each workpiece 70.

When a molten shape abnormality occurs, as illustrated in part (A) of FIG. 6, a signal having a waveform including a peak showing a temporal increase in signal intensity is obtained, in contrast to the normal waveform in part (B) in FIG. 6. The peak of the signal due to occurrence of a molten shape abnormality is due to, for example, light emission of foreign substance 80 that causes the abnormality. The occurrence of the molten shape abnormality may cause a temporal attenuation peak due to an instantaneous attenuation of light emission of foreign substance 80. In this case, a signal having a waveform including a temporal attenuation peak of signal intensity is obtained. Even in such a case, a local minimum value can be extracted in the flow illustrated in the flowchart in FIG. 5, described later, and an integrated value can be calculated for a value obtained by subtracting the average Sa from the signal intensity in section Tp. The following flow will be described as an example for a signal of which waveform includes a peak of a temporal increase in signal intensity.

In the flowchart in FIG. 5, CPU 51 then calculates from the obtained signal a feature quantity to be input to determination model 57 (S2). In the present exemplary embodiment, CPU 51 calculates, as a feature quantity, an intensity value (hereinafter, referred to as "peak intensity value") based on signal intensity at the peak in addition to a signal intensity to which preprocessing such as normalization is applied.

Figure 7:
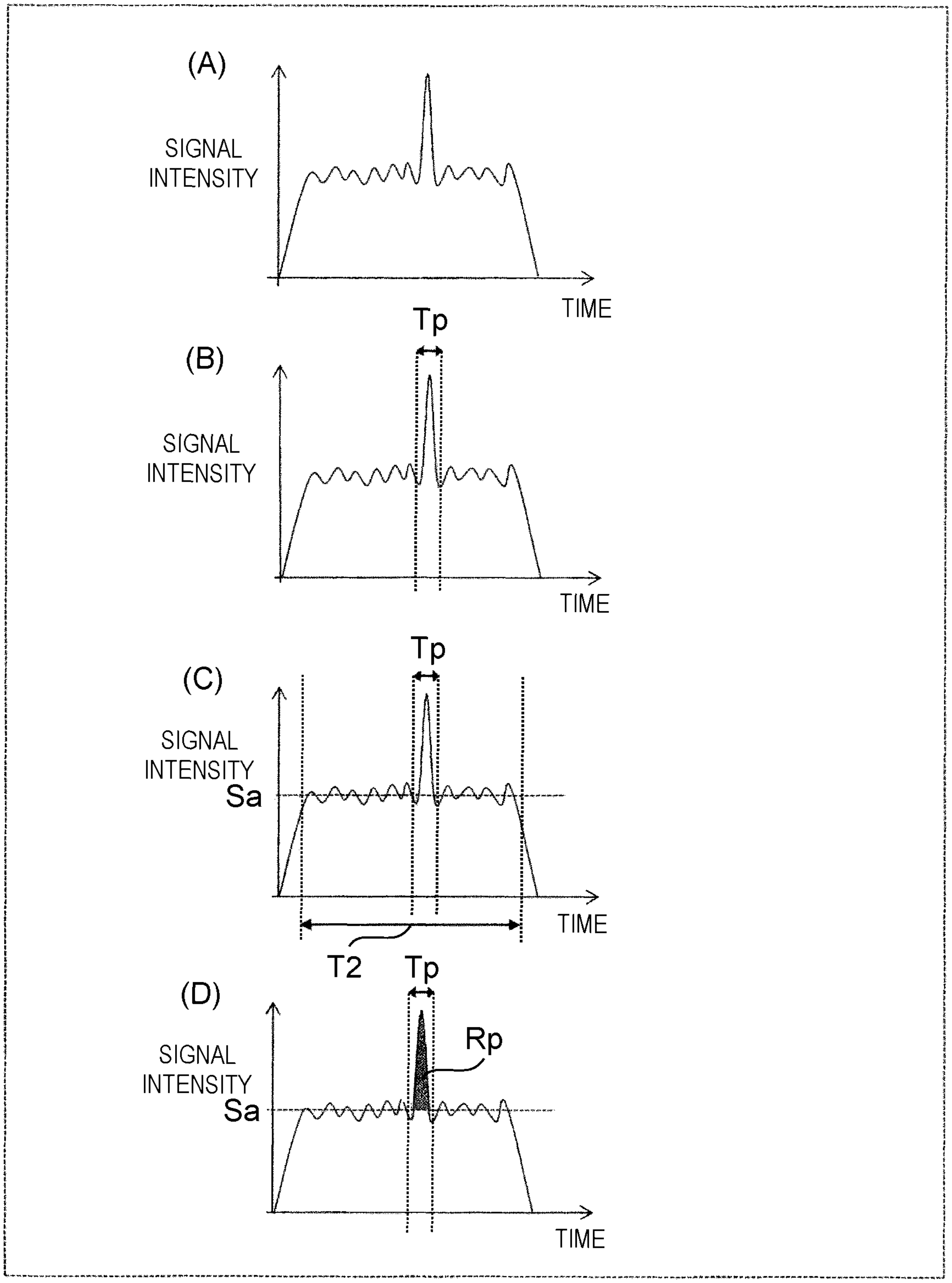
FIG. 7 is a diagram for explaining a process of calculating a feature quantity in the determination device.

FIG. 7 is a diagram for explaining the process (S2) of calculating a feature quantity performed by determination device 50. Part (A) of FIG. 7 illustrates, like in part (A) of FIG. 6, a temporal change in signal intensity of a signal corresponding to heat radiation, visible light, or reflected light generated when molten shape abnormality occurs. A process of calculating the feature quantity of peak intensity value in step S2 in FIG. 5 will be described with reference to FIG. 7.

First, CPU 51 performs a process of detecting a peak of an obtained signal. For example, CPU 51 performs calculation of comparing values of signal intensity among sampling periods and extracts a point having a larger value than the points that are temporally immediately before and after as a local maximum value. In this extraction, a threshold may be set from a viewpoint of narrowing the range of a value extracted as a local maximum value to a predetermined signal intensity or more. For example, CPU 51 extracts a local minimum value of signal intensity in a manner similar to that for a local maximum value, and detects a peak as a region of signal waveform in section Tp sandwiched between two points adjacent to the local maximum value. Section Tp corresponds to the time in which the peak occurs. Part (B) of FIG. 7 illustrates an example in which a peak in section Tp in the signal in part (A) of FIG. 7 is detected.

After detection of the peak, CPU 51 calculates average Sa of signal intensity not including the peak. Average Sa is calculated, for example, as an average of signal intensity in time (T2−Tp) obtained by excluding section Tp from time T2 of the peak output for a single pulse of laser beam 6. Part (C) of FIG. 7 illustrates an example in which average Sa is calculated for the example in part (B) of FIG. 7.

Subsequently, CPU 51 calculates, as a peak intensity value, an integrated value calculated for the value obtained by subtracting average Sa of signal intensity not including the peak from the signal intensity in section Tp corresponding to the time where peak occurs. Part (D) of FIG. 7 illustrates an example of calculating the integrated value for the example in part (C) of FIG. 7. The integrated value corresponds to an area of region Rp illustrated in part (D) of FIG. 7.

After the calculation of the feature quantity as described above (S2), CPU 51 performs a determination model process (S3) for determining the position, number, and size of molten shape abnormality by inputting the feature quantity to determination model 57. The feature quantity of signal intensity is input to determination model 57 as, for example, an amplitude of a signal waveform for each sampling period for A/D conversion.

Figure 8:
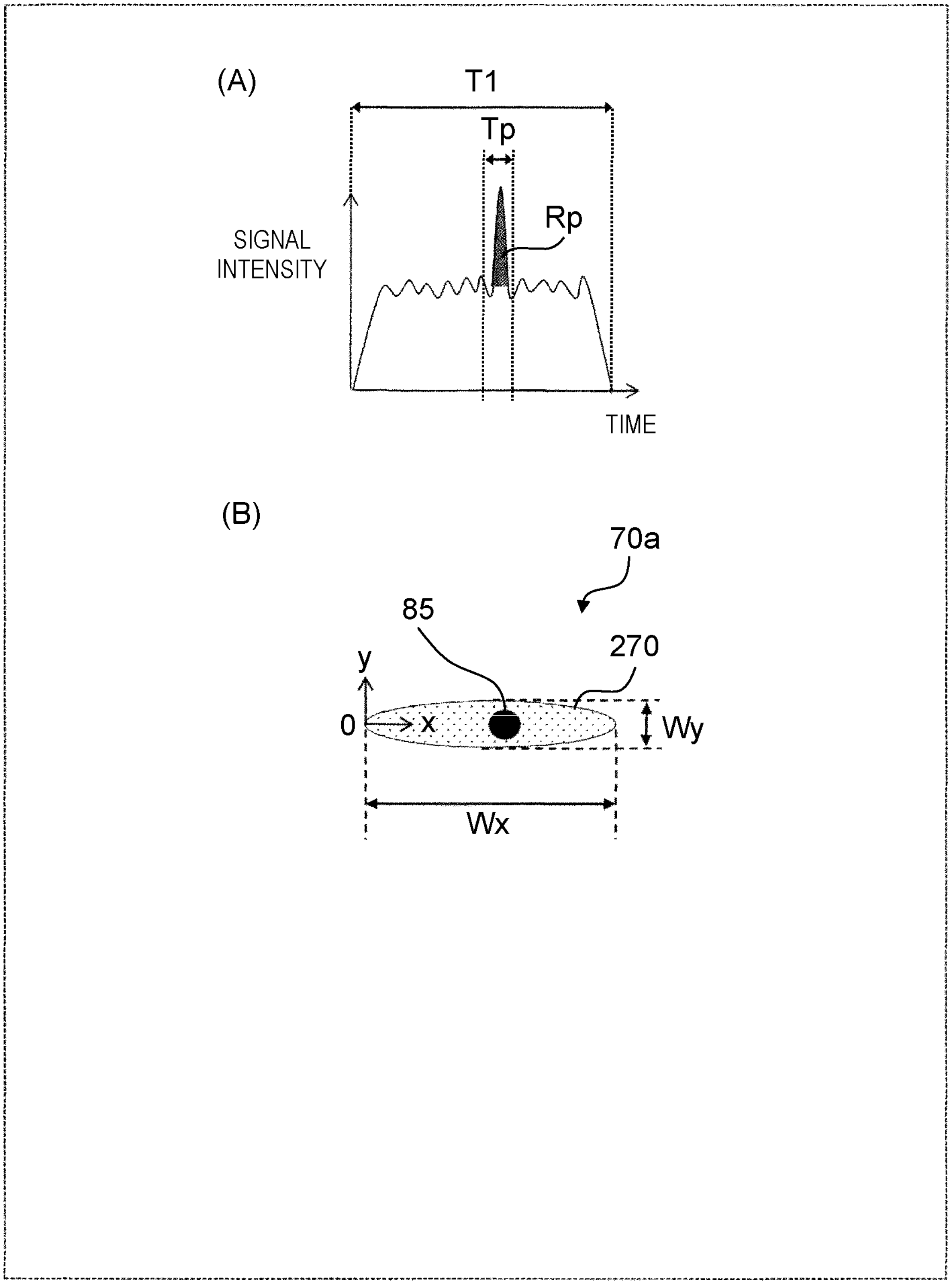
FIG. 8 is a diagram for explaining a determination model process in the determination device.

FIG. 8 is a diagram for explaining the determination model process (S3). Part (A) of FIG. 8 illustrates a signal waveform when molten shape abnormality occurs like in part (A) of FIG. 6. Part (B) of FIG. 8 schematically illustrates an appearance of member 70*a* of workpiece 70 on the side to laser processing device 30 after processing in which the signal in part (A) of FIG. 8 is generated. In part (B) of FIG. 8, hole 85 is formed as an example of molten shape abnormality in welded region 270 having molten length Wx and molten width Wy.

Laser processing device 30 according to the present exemplary embodiment performs welding over molten length Wx for each workpiece 70 in time T1 corresponding to a single pulse. In the example in part (A) of FIG. 8, the peak in section Tp occurs corresponding to forming of hole 85 when laser processing device 30 progresses the processing in the positive direction of an x axis in part (B) of FIG. 8, and is detected in step S2.

In the example in FIG. 8, in the determination model process (S3), CPU 51 determines the position, number, and size of hole 85 in part (B) of FIG. 8 by inputting the feature quantities of signal intensity and peak intensity value calculated from the signal in part (A) of FIG. 8 to determination model 57. The position is determined as coordinates of the center of gravity of hole 85, for example, in an orthogonal coordinate system of which origin is on the start point of welding on member 70*a*. The size is determined, for example, as an area of hole 85. The number is determined as "1" since there is no molten shape abnormality other than hole 85 in part (B) of FIG. 8.

Referring back to FIG. 5, CPU 51 outputs the determination result of the position, number, and size of molten shape abnormality such as hole 85 by communication circuit 52 (S4). The determination result can be received and displayed by, for example, an external information processing device or a display device. Determination device 50 may include a display device (for example, a display) capable of communicating with CPU 51 and display the determination result on the display device.

Then, CPU 51 ends the flowchart in FIG. 5. The flowchart in FIG. 5 is repetitively executed, for example, when welding processing is performed for each workpiece 70.

According to the above determination process, determination device 50 of the present exemplary embodiment obtains a signal generated by optical sensor 22 of spectral device 40 (S1), calculates a feature quantity from the signal (S2), and determines the position, number, and size of molten shape abnormality by determination model 57 based on the feature quantity (S3). Accordingly, determination device 50 can determine in detail the processing state related to molten shape abnormality in laser processing for lap welding.

In step S2 in FIG. 5, the feature quantity may be calculated for all the heat radiation, visible light, and reflected light, or may be calculated only for any one of heat radiation, visible light, and reflected light. In the determination model process (S3), determination model 57 may determine, for example, only the position and number of molten shape abnormality.

In addition, in step S2, the attenuation peak described above may also be detected to calculate an integrated value of signal intensity. In this case, while the value of the attenuation peak is negative, the peak intensity value calculated for the increase peak described in the example in FIG.

7 is positive. In this way, the peak of attenuation and the peak of increase of signal intensity can be distinguished from each other, and a change in light emission by foreign substance 80 can be reflected in the feature quantity. This is not the only way for a case when an attenuation peak is detected. For example, focusing only on the existence and magnitude of a peak, the integrated value of signal intensity of the peak may be used as a feature quantity.

2-2. Training Process

A training process for constructing determination model 57 will be described below with reference to FIGS. 9 and 10.

Figure 9:
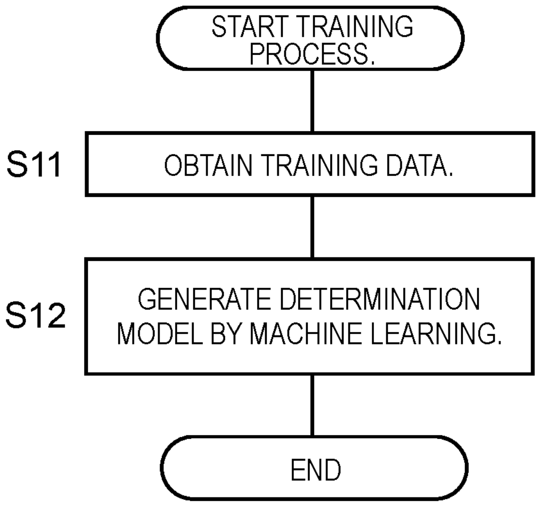
FIG. 9 is a flowchart illustrating a training process for the determination model.

FIG. 9 is a flowchart illustrating a training process for determination model 57. Each process in the flowchart is executed by, for example, CPU 51 of determination device 50.

First, CPU 51 obtains, for example, training data previously stored in storage device 53 (S11).

Training data is data in which feature quantities such as signal intensities and peak intensity values of heat radiation, visible light, and reflected light are associated with the position, number, and size of molten shape abnormality as a processing state. The training data is constructed by recording, in association with each other, feature quantities calculated from signals based on heat radiation, visible light, and reflected light detected during laser processing under a plurality of conditions in which the processing state changes, and the processing state determined by appearance measurement of welded region 270 after the processing. The appearance measurement may be performed by, for example, observation of welded region 270 using an optical microscope or measurement of an image obtained by photographing welded region 270, but is not particularly limited to such ways.

Figure 10:
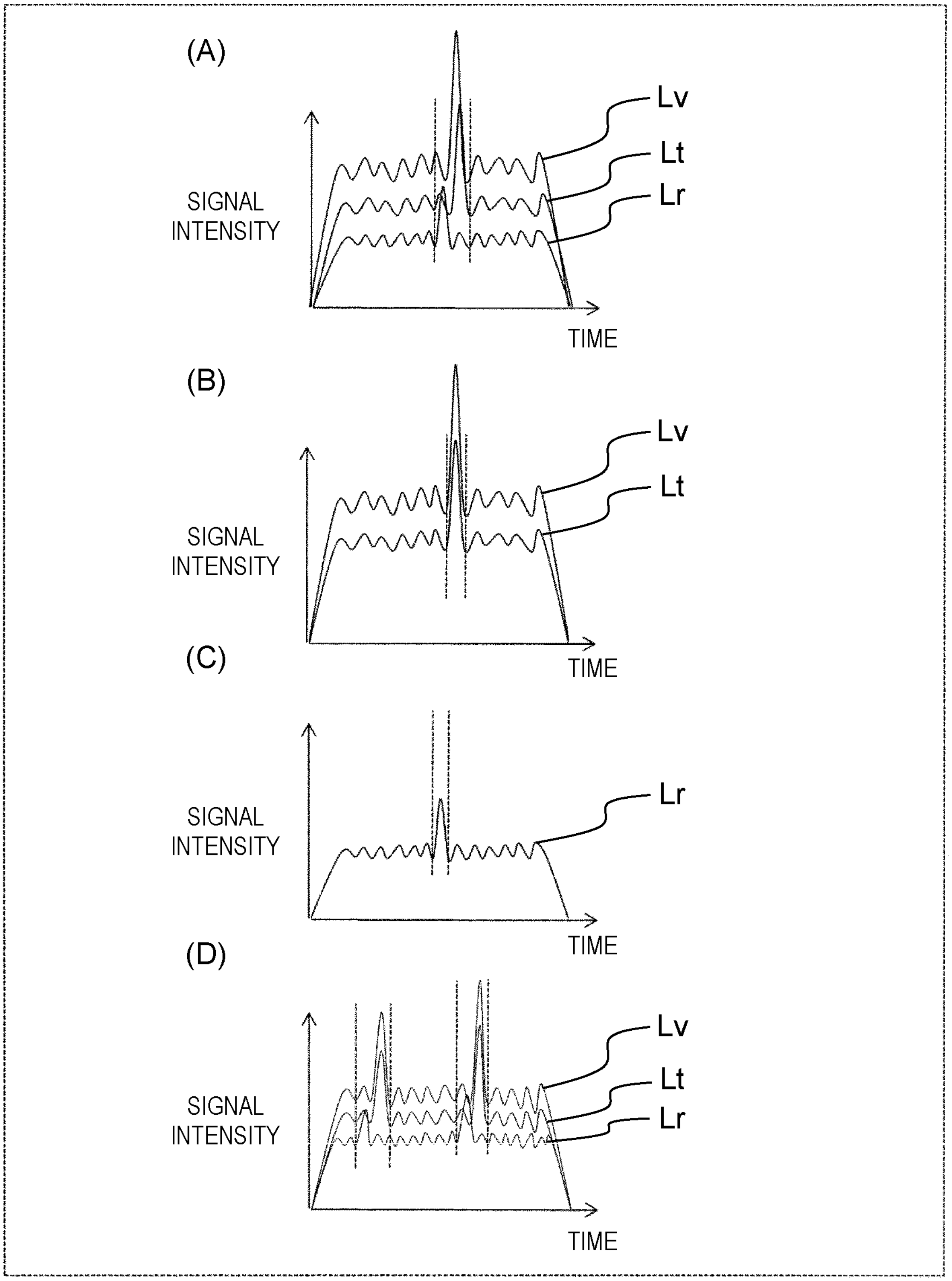
FIG. 10 is a diagram for explaining a signal generated when molten shape abnormality occurs.

FIG. 10 is a diagram for explaining a signal generated when molten shape abnormality occurs. When constructing the training data, feature quantities based on signals having various waveform patterns as illustrated in FIG. 10 and the corresponding processing state are collected.

In part (A) of FIG. 10, a peak corresponding to a single molten shape abnormality is detected in every one of signals Lt, Lv, and Lr respectively generated depending on intensities of heat radiation, visible light, and reflected light. In part (B) of FIG. 10, a peak of a single molten shape abnormality is detected in two signals Lt, Lv of heat radiation and visible light. In part (C) of FIG. 10, a peak of a single molten shape abnormality is detected only in signal Lr of reflected light. In part (D) of FIG. 10, two peaks corresponding to two molten shape abnormalities are detected in each of signals Lt, Lv, Lr of heat radiation, visible light, and reflected light, respectively. As illustrated in parts (A) and (D) of FIG. 10, signal Lr of reflected light tends to have a peak occurring earlier than signals Lt, Lv of heat radiation and visible light.

Including the feature quantities based on signals having various patterns of peak detection, as described above, and the processing state corresponding to the feature quantities in the training data makes it possible to generate determination model 57 capable of determining the processing state in detail even when conditions, such as the light in which a peak occurs, the time when a peak occurs, and the number of peaks, change by the processing described later. In the present exemplary embodiment, using the feature quantities based on three lights, that are, heat radiation, visible light, and reflected light makes it possible to reflect the tendency of occurrence of molten shape abnormality in determination model 57 even when a peak is detected only in one or two signals of heat radiation, visible light, and reflected light. For example, data including two or less peaks, which are assumed in actual processing, is used as the training data, but the number of peaks is not particularly limited to two or less. Data including three or more peaks may be used. A time section regarded to include a single peak may be set in advance.

On obtaining the training data (S1), CPU 51 performs machine learning using the training data and generates determination model 57 (S2). Determination model 57 is generated as a regression model based on, for example, a random forest or a neural network.

According to the above training process, determination model 57 can be generated as a learned model that determines the position, number, and size of molten shape abnormality from the feature quantities based on signals corresponding to heat radiation, visible light, and reflected light detected during laser processing.

Note that, the training process for determination model 57 may be performed in an information processing device other than determination device 50. Determination device 50 may obtain an already constructed determination model by communication circuit 52 via, for example, a communication network.

In addition, the training data for determination model 57 may include a feature quantity of a case where no molten shape abnormality occurs and a processing state of a case where no molten shape abnormality occurs. The feature quantity of a case where no molten shape abnormality occurs may be, for example, a peak intensity value of "0". The processing state of a case where no molten shape abnormality occurs may be, for example, position "0", number "0", and size "0" of molten shape abnormality.

3. Effects

As described above, in the present exemplary embodiment, the determination process (S1 to S4) provides a determination method for determining the processing state in laser processing for lap welding. The present method includes detecting, using optical sensor 22, at least one of heat radiation (heat radiation light), visible light, and reflected light generated at molten portion 27 (an example of welded portion) formed at a surface of workpiece 70 by emission of laser beam 6 on workpiece 70, obtaining, from optical sensor 22, a signal indicating a change in heat radiation, visible light, and reflected light in time T1 (time section) corresponding to a welding time of each workpiece 70 (S1), determining, as the processing state, the position and number of molten shape abnormality in welded region 270 having molten length Wx and molten width Wy by inputting a feature quantity to determination model 57 that determines the processing state (S2, S3), the feature quantity including signal intensity of the signal based on the signal, the molten shape abnormality occurring when foreign substance 80 exists at an overlapping surface of workpiece 70, and outputting, as a determination result, the determined position and number of molten shape abnormality (S4). Determination model 57 is constructed based on training data including the feature quantity calculated under a condition where the molten shape abnormality occurs and the processing state in the condition where the molten shape abnormality occurs.

According to the method described above, the signal that is based on one or more of heat radiation, visible light, and reflected light generated by emission of laser beam 6 and detected is obtained (S1), a feature quantity including signal intensity is calculated, and the position and number of molten shape abnormality are determined as the processing state (S2, S3). Accordingly, the processing state related to the molten shape abnormality can be determined in detail based on the signal intensity of at least one of heat radiation, visible light, and reflected light detected in laser processing for lap welding.

In the present exemplary embodiment, the determination step (S2, S3) further includes detecting a peak of a signal to determine a size of molten shape abnormality as the processing state. The output step (S4) further includes outputting the determined size of the molten shape abnormality as the determination result. The feature quantity includes a peak intensity value that is an example of an intensity value based on the signal intensity of the signal at the peak. Accordingly, the processing state, including the size of molten shape abnormality, can be determined in more detail based on the peak intensity value.

In the present exemplary embodiment, the intensity value is an integrated value obtained by integrating the difference value for section Tp (time in which the peak occurs), the difference value being obtained by subtracting average Sa of signal intensity of the signal not including the peak from the signal intensity of the peak (see FIG. 7). This makes it easy to determine the processing state such as the size of molten shape abnormality in detail by reflecting the intensity of light emission caused by occurrence of molten shape abnormality due to foreign substance 80 in the feature quantity.

In the present exemplary embodiment, determination model 57 includes a learned model generated by machine learning using training data in which a feature quantity calculated from a signal based on at least one of heat radiation, visible light, and reflected light detected during laser processing under each condition of a plurality of conditions in which the processing state changes is associated with the processing state determined by appearance measurement of welded region 270. Accordingly, determination model 57 that determines the processing state is obtained from the feature quantity based on at least one of heat radiation, visible light, and reflected light.

In determination system 100 of the present exemplary embodiment, determination device 50 is an example of a determination device for determining the processing state in laser processing for lap welding. Determination device 50 includes CPU 51 as an example of an arithmetic circuit, and communication circuit 52. Communication circuit 52 receives a signal generated by optical sensor 22 detecting at least one of heat radiation (heat radiation light), visible light, and reflected light generated at molten portion 27 (an example of a welded portion) formed at a surface of workpiece 70 by emission of laser beam 6 on workpiece 70. The signal indicates a change in at least one of heat radiation, visible light, and reflected light in time T1 as an example of a time section corresponding to the welding time of each workpiece 70. CPU 51 obtains a signal by communication circuit 52 (S1), determines, as the processing state, the position and number of molten shape abnormality in welded region 270 having molten length Wx and molten width Wy by inputting a feature quantity including signal intensity of the signal based on the signal to determination model 57 that determines the processing state (S2, S3), the molten shape abnormality occurring when foreign substance 80 exists at an overlapping surface of workpieces 70, and outputs by communication circuit 52, as a determination result, the determined position and number of molten shape abnormality (S4). Determination model 57 is constructed based on training data including the feature quantity calculated under a condition where the molten shape abnormality occurs and the processing state in the condition where the molten shape abnormality occurs.

According to determination device 50 described above, the processing state in laser processing for lap welding can be determined in detail by performing the determination method described above.

Other Exemplary Embodiments

As described above, the exemplary embodiment has been described as an example of the art disclosed in the present application. The art according to the present disclosure is, however, not limited to the above exemplary embodiment, and is applicable to other exemplary embodiments suitably made by modification, replacement, addition, or omission, for example. Furthermore, a different exemplary embodiment can also be made by a combination of the components of the exemplary embodiments described above.

In the first exemplary embodiment, determination device 50 calculates the feature quantities of signal intensity and peak intensity value in the determination process (S2 in FIG. 5). In the present exemplary embodiment, step S2 may be that the peak intensity value is not calculated and only the signal intensity is used as the feature quantity.

In the first exemplary embodiment, determination device 50 obtains a signal corresponding to heat radiation, visible light, and reflected light detected by optical sensor 22 of spectral device 40 (S1). In the present exemplary embodiment, determination device 50 may obtain a signal for only one or two of heat radiation, visible light, and reflected light. In this case, in steps S2 to S3, a feature quantity is calculated for a signal of only one or two of heat radiation, visible light, and reflected light, and is input to determination model 57. In the present exemplary embodiment, determination model 57 may be constructed using, as training data, a feature quantity based on a signal of only one or two of heat radiation, visible light, and reflected light and a processing state.

In the first exemplary embodiment, determination model 57 is constructed using a feature quantity such as signal intensity and the position, number, and size of molten shape abnormality as training data (S11 to S12). In the present exemplary embodiment, determination model 57 may be constructed using a feature quantity and the position and number of molten shape abnormality as training data. In this case, determination device determines the position and number of molten shape abnormality as the processing state in the determination process (S1 to S4).

According to the determination method and the determination device of the present disclosure, the processing state can be determined in detail for, in particular, molten shape abnormality occurring in a welded region in laser processing for lap welding.

The present disclosure is not limited to the exemplary embodiments described above, and various modifications can be made. That is, exemplary embodiments obtained by combining technical means suitably modified by those skilled in the art also fall within the scope of the present disclosure.

INDUSTRIAL APPLICABILITY

The present disclosure is applicable to a determination system for determining a processing state in laser processing for lap welding, in particular, to a method and a device for determining molten shape abnormality in a welded portion.

REFERENCE MARKS IN THE DRAWINGS

1: laser oscillator
2: laser transmission fiber

3: lens barrel
4: collimating lens
11: condenser lens
6: laser beam
7: first mirror
8: second mirror
13: optical fiber
15: collimating lens
16: third mirror
17: fourth mirror
18: fifth mirror
19, 20, 21: condenser lens
22: optical sensor
23: transmission cable
24: controller
26: hold jig
27: molten portion
30: laser processing device
40: spectral device
50: determination device
51: CPU
52: communication circuit
53: storage device
56: control program
57: determination model
70: workpiece
70*b*: member
85: hole
100: determination system
270: welded region

The invention claimed is:

1. A determination method for determining a processing state in laser processing for lap welding, the determination method comprising:

detecting, using an optical sensor, at least one of heat radiation light, visible light, and reflected light generated at a welded portion formed at a surface of a workpiece by emission of a laser beam on the workpiece;

obtaining, from the optical sensor, a signal indicating a change in the at least one of heat radiation light, visible light, and reflected light in a time section corresponding to a welding time of the workpiece;

determining, as the processing state, a position and a quantity of molten shape abnormalities in a welded region having a molten length and a molten width by inputting a feature quantity to a determination model that determines the processing state, the feature quantity including signal intensity of the signal based on the signal, the molten shape abnormalities occurring when a foreign substance exists at an overlapping surface of the workpiece; and outputting, as a determination result, the position and the number of the molten shape abnormalities that are determined, wherein the determination model is constructed based on training data including the feature quantity calculated under a condition where the molten shape abnormalities occur and the processing state in the condition where the molten shape abnormalities occur, and wherein the feature quantity further includes an integrated value obtained by detecting a peak included in the signal, and integrating a difference value obtained by subtracting an average value of signal intensity of the signal excluding the peak from the signal intensity of the peak over a time period during which the peak occurs.

2. The determination method according to claim 1, wherein:

the determining includes determining a size of the molten shape abnormalities as the processing state, the outputting includes outputting the size of the determined molten shape abnormalities as the determination result, and the feature quantity further includes an intensity value based on the signal intensity of the signal at the peak.

3. The determination method according to claim 2, wherein the intensity value is an integrated value obtained by integrating a difference value for a time in which the peak occurs, the difference value being obtained by subtracting an average of the signal intensity of the signal not including the peak from signal intensity of the peak.

4. The determination method according to claim 1, wherein the determination model includes a learned model generated by machine learning using training data, the training data including (i) a feature quantity calculated from a signal based on the at least one of heat radiation light, visible light, and reflected light detected during the laser processing under each condition of a plurality of conditions where the processing state changes and (ii) the processing state that is determined by appearance measurement of the welded region, the feature quantity, and the processing state being associated with each other.

5. A determination device for determining a processing state in laser processing for lap welding, the determination device comprising:

an arithmetic circuit; and a communication circuit configured to receive a signal generated by an optical sensor detecting at least one of heat radiation light, visible light, and reflected light generated at a welded portion formed at a surface of a workpiece by emission of a laser beam on the workpiece, wherein the signal indicates a change in the at least one of heat radiation light, visible light, and reflected light in a time section corresponding to a welding time of the workpiece, wherein the arithmetic circuit is configured to:

obtain the signal from the communication circuit, determine as the processing state a position and a number of molten shape abnormalities in a welded region having a molten length and a molten width, the determining performed by inputting a feature quantity to a determination model that determines the processing state, the feature quantity including a signal intensity of the signal based on the signal, the molten shape abnormalities occurring when a foreign substance exists at an overlapping surface of the workpiece, and output by the communication circuit, as a determination result, the position and the number of the determined molten shape abnormalities, and wherein the determination model is constructed based on training data including the feature quantity calculated under a condition where the molten shape abnormalities occur, and the processing state in the condition where the molten shape abnormalities occur, and wherein the feature quantity further includes an integrated value obtained by detecting a peak included in the signal, and integrating a difference value obtained by subtracting an average value of signal intensity of the signal excluding the peak from the signal intensity of the peak over a time period during which the peak occurs.

6. The determination device according to claim 5, wherein:

the arithmetic circuit is configured to:

detect a peak in the signal and determine a size of the molten shape abnormalities as the processing state, and outputting by the communication circuit the size of the determined molten shape abnormalities as the determination result, and the feature quantity includes an intensity value based on the signal intensity of the signal at the peak.

7. The determination device according to claim 6, wherein the intensity value is an integrated value obtained by integrating a difference value for a time during which the peak occurs, the difference value being obtained by subtracting an average of the signal intensity of the signal not including the peak from signal intensity of the peak.

8. The determination device according to claim 5, wherein the determination model includes a learned model generated by machine learning using training data, the training data including (i) a feature quantity calculated from a signal based on the at least one of heat radiation light, visible light, and reflected light detected during the laser processing under each condition of a plurality of conditions where the processing state changes and (ii) the processing state determined by appearance measurement of the welded region, the feature quantity and the processing state being associated with each other.

* * * * *